United States Patent
Peng et al.

(10) Patent No.: US 9,412,163 B2
(45) Date of Patent: Aug. 9, 2016

(54) METHOD FOR DETECTING AND QUANTIFYING CEREBRAL INFARCT

(71) Applicants: National Central University, Taoyuan (TW); Huan-Cheng Chang, Taoyuan (TW)

(72) Inventors: Syu-Jyun Peng, Hsinchu County (TW); Jang-Zern Tsai, Taoyuan (TW); Yu-Wei Chen, Taoyuan (TW); Kuo-Wei Wang, Taoyuan (TW)

(73) Assignees: National Central University, Taoyuan (TW); Huan-Cheng Chang, Taoyuan (TW)

( * ) Notice: Subject to any disclaimer, the term of this patent is extended or adjusted under 35 U.S.C. 154(b) by 37 days.

(21) Appl. No.: 14/642,761

(22) Filed: Mar. 10, 2015

(65) Prior Publication Data

US 2016/0035085 A1 Feb. 4, 2016

(30) Foreign Application Priority Data

Jul. 31, 2014 (TW) .............................. 103126232 A

(51) Int. Cl.
*G06T 7/00* (2006.01)
*A61B 5/00* (2006.01)

(52) U.S. Cl.
CPC ............. *G06T 7/0012* (2013.01); *A61B 5/0042* (2013.01); *G06T 7/0081* (2013.01); *G06T 2207/10088* (2013.01); *G06T 2207/20148* (2013.01); *G06T 2207/30016* (2013.01)

(58) Field of Classification Search
None
See application file for complete search history.

(56) References Cited

U.S. PATENT DOCUMENTS 6,366,797 B1 4/2002 Fisher et al.
8,125,223 B2 2/2012 K.N. et al.

FOREIGN PATENT DOCUMENTS

CN 1270005 A 10/2000
CN 102016922 A 4/2011

OTHER PUBLICATIONS

Ridgway, Gerard. "Issues with Threshold Masking in Voxel-Based Morphometry of Atrophied Brains." Neuroimage. 44 (Jan. 2009): 99-101. Accessed Jun. 9, 2016. http://www.sciencedirect.com/science/article/pii/S1053811908009786.*
K. N. Bhanu Prakash et al., "Automatic processing of diffusion-weighted ischemic stroke images based on divergence measures: slice and hemisphere identification, and stroke region segmentation", published online: Oct. 21, 2008, Int J Cars (2008) 3:559-570, DOI10.1007/s11548-008-0260-3.

(Continued)

*Primary Examiner* — Utpal Shah
*Assistant Examiner* — Kate R Duffy
(74) *Attorney, Agent, or Firm* — CKC & Partners Co., Ltd.

(57) ABSTRACT

A method for detecting a cerebral infarct includes receiving an image of a brain of a subject from a magnetic resonance imaging scanner, wherein the image has a plurality of voxels, and each of the voxels has a voxel intensity. Then, the voxel intensities are normalized, wherein the normalized voxel intensities have a distribution peak, and the normalized voxel intensity of the distribution peak is $I_{peak}$. A threshold is determined, which is the $I_{peak}$+ a value. Voxel having the normalized voxel intensity larger than the threshold is selected, wherein the selected voxel is the cerebral infarct. A method for quantifying the cerebral infarct is also provided.

17 Claims, 10 Drawing Sheets

(56) References Cited

OTHER PUBLICATIONS

Wu Li et al., "Robust unsupervised segmentation of infarct lesion from diffusion tensor MR images using multiscale statistical classification and partial volume voxel reclassification", NeuroImage 23 (2004) 1507-1518, doi:10.1016/j.neuroimage.2004.08.009.

Bhanu Prakash KN et al., "Identification, Segmentation, and image Property Study of Acute Infarcts in Diffusion-Weighted Images by Using a Probabilistic Neural Network and Adaptive Gaussian Mixture Model", Acad Radiol 2006; 13:1474-1484.

Nidiyare Hevia-Montiel et al., "Robust Nonparametric Segmentation of Infarct Lesion from Diffusion-Weighted MR Images", Conference of the IEEE EMBS, Aug. 23-26, 2007: 2102-2105.

Varsha Gupta et al, "Automatic and Rapid Identification of Infarct Slices and Hemisphere in DWI Scans" Acad Radiol 2008; 15:24-39.

Shan Shen et al., "Detection of Infarct Lesions From Single MRI Modality Using Inconsistency Between Voxel Intensity and Spatial Location—A 3-D Automatic Approach", IEEE Transactions on Information Technology in Biomedicine, vol. 12, No. Jul. 4, 2008: 532-540.

Wu Li, et al, "Automatic segmentation of brain infarction in diffusion-weighted MR images", Proceedings of SPIE vol. 5032 (2003): 1531-1542.

Jang-Zern Tsai et al., "Automatic Detection and Quantification of Acute Cerebral Infarct by Fuzzy Clustering and Histographic Characterization on Diffusion Weighted MR Imaging and Apparent Diffusion Coefficient Map", Hindawi Publishing Corporation, BioMed Research International, vol. 2014, Article ID 963032, 13 pages, http://dx.doi.org/10.1155/2014/963032, Published Mar. 12, 2014.

* cited by examiner

METHOD FOR DETECTING AND QUANTIFYING CEREBRAL INFARCT

RELATED APPLICATIONS

This application claims priority to Taiwanese Application Serial Number 103126232, filed Jul. 31, 2014, which is herein incorporated by reference.

BACKGROUND

1. Field of Invention

The present invention relates to methods for detecting and quantifying a cerebral infarct. More particularly, the present invention relates to automatic methods for detecting and quantifying a cerebral infarct.

2. Description of Related Art

In recent years, the stroke incidence and mortality of people remain high, and the stroke has been ranked as the top 10 causes of death, indicating that the stroke is a major threat to people's health. The stroke is the loss of brain function due to a disturbance in the blood supply to the brain, which is caused by ischemia, i.e. lack of blood flow, or hemorrhage. Ischemic stroke is caused by thrombotic or embolic occlusion of a cerebral artery, and hemorrhagic stroke is caused by bleeding into the brain. In clinical, most stroke patients suffer from the ischemic stroke, and generally have cerebral infarct.

There are two major medical methods for detecting a cerebral infarct, which are computed tomography (CT) and magnetic resonance imaging (MRI), and MRI is more widely used among the two. The signal of MRI comes from the resonance of hydrogen atoms presented in water molecules inside the brain. When infarct caused by ischemia occurred, water molecules inside the brain tissue change, and thereby MRI can detect the changes of signal intensity, which is applied in the detection and treatment for cerebral infarct. With the progress of MRI technology, in addition to traditional images, such as T1-weighted image, that can understand anatomical structure of tissue, the delicate structure of tissue and its functional components can be further understood by diffusion-weighted imaging (DWI).

The method for detecting acute cerebral infarct in hospital is semi-automatic segmentation method assisted by software, which is time-consuming for processing and analysis, and is prone to produce variability between different raters, i.e. doctors. Automatic algorithms for segmentation of cerebral infarct have been proposed in the past, such as Li et al. "Robust unsupervised segmentation of infarct lesion from diffusion tensor MR images using multiscale statistical classification and partial volume voxel reclassification." *Neuroimage.* 2004 December; 23(4):1507-18, Prakash et al. "Identification, segmentation, and image property study of acute infarcts in diffusion-weighted images by using a probabilistic neural network and adaptive gaussian mixture model." *Acad Radiol.* 2006 December; 13(12):1474-84, and Shen et al. "Detection of infarct lesions from single MRI modality using inconsistency between voxel intensity and spatial location—a 3-D automatic approach." *IEEE Trans Inf Technol Biomed.* 2008 July; 12(4):532-40. However, it is difficult to accurately detect the cerebral infarct by using these methods due to noise, signal overlap, partial volume effect (PVE), and artifacts caused by magnetic inhomogeneity.

Therefore, there is a need for methods for detecting and quantifying cerebral infarct, which can not only reduce the variability of human judgment but also detect the cerebral infarct rapidly and accurately, especially for acute cerebral infarct, which needs a rapid, real-time, and accurate detecting method.

SUMMARY

An aspect of the present invention provides a method for detecting a cerebral infarct, which can detect the cerebral infarct automatically. The method includes receiving an image of a brain of a subject from a magnetic resonance imaging scanner, wherein the image has a plurality of voxels, and each of the voxels has a voxel intensity. Next, the voxel intensities are normalized to make the voxel intensities disperse in a standard range, wherein the normalized voxel intensities have a distribution peak, and the normalized voxel intensity of the distribution peak is $I_{peak}$. A threshold is determined, which is the $I_{peak}$+ a value. The value is a difference value between a minimum normalized voxel intensity of the cerebral infarct diagnosed by a semi-automatic segmentation method and the $I_{peak}$. Then, voxel having the normalized voxel intensity larger than the threshold is selected, wherein the selected voxel is the cerebral infarct.

According to one embodiment of the present invention, receiving the image of the brain of the subject from the magnetic resonance imaging scanner comprises determining a brain mask of the subject in the image. The brain mask may include an inner surface and an outer surface of a skull of the subject.

According to one embodiment of the present invention, the image is obtained by diffusion-weighted imaging (DWI).

According to one embodiment of the present invention, the standard range is (0, 1).

According to one embodiment of the present invention, the method for detecting a cerebral infarct further includes forming a normalized voxel intensity histogram having the $I_{peak}$ from the normalized voxel intensities. Then, the normalized voxel intensity histogram is filtered by a wave filter.

According to one embodiment of the present invention, the value is 0.1-0.31, preferably 0.2.

According to one embodiment of the present invention, before selecting the voxel having the normalized voxel intensity larger than the threshold, the method for detecting a cerebral infarct further includes pre-screening the voxels, which eliminates voxel with the normalized voxel intensity smaller than or equal to the $I_{peak}$. Then, a fuzzy C-mean clustering is performed on the pre-screened voxels to form a plurality of voxel clusters, wherein each of the voxel clusters has a first average normalized voxel intensity.

According to one embodiment of the present invention, selecting the voxel with the normalized voxel intensity larger than the threshold includes selecting voxel cluster having the first average normalized voxel intensity larger than the threshold to form a candidate voxel cluster. Next, the candidate voxel cluster is further divided into at least one voxel label, wherein the voxel label has a second average normalized voxel intensity. Then, voxel label having the second average normalized voxel intensity larger than the threshold is selected to form a candidate voxel label, wherein the candidate voxel label is the cerebral infarct.

According to one embodiment of the present invention, the voxel clusters includes 6-100 voxel clusters, preferably 50 voxel clusters.

According to one embodiment of the present invention, the candidate voxel cluster further divided into the voxel label is based on the location of the voxel label.

According to one embodiment of the present invention, forming the candidate voxel label further includes determining an edge of each voxel label in the image, and eliminating voxel label without the edge to form the candidate voxel label.

According to one embodiment of the present invention, the method for detecting a cerebral infarct further includes receiving an apparent diffusion coefficient (ADC) map of the brain of the subject from the magnetic resonance imaging scanner, wherein the ADC map has a plurality of ADC voxels, and each of the ADC voxels has an ADC voxel intensity. Then the ADC map is registered to the corresponding image by a rigid registration, and calibrated. The method continues with normalizing the ADC voxel intensities to make the ADC voxel intensities disperse in a standard range, and to form a normalized ADC voxel intensity histogram. In one embodiment, forming the candidate voxel label further includes determining a peak of the normalized ADC voxel intensity histogram, which the normalized ADC voxel intensity of the peak is $I_{peak, ADC}$, and an average normalized ADC voxel intensity of lower half in the voxel label, $I_{lower\ mean, ADC}$. Then, voxel label with $I_{lower\ mean, ADC}/I_{peak, ADC} \geq 0.5$ is eliminated to form the candidate voxel label.

Another aspect of the present invention provides a method for quantifying a cerebral infarct, including determining the cerebral infarct of an image by the aforementioned method. Then, cerebral infarct volume is determined based on the cerebral infarct.

BRIEF DESCRIPTION OF THE DRAWINGS

The invention can be more fully understood by reading the following detailed description of the embodiment, with reference made to the accompanying drawings as follows.

DETAILED DESCRIPTION

Figure 1:
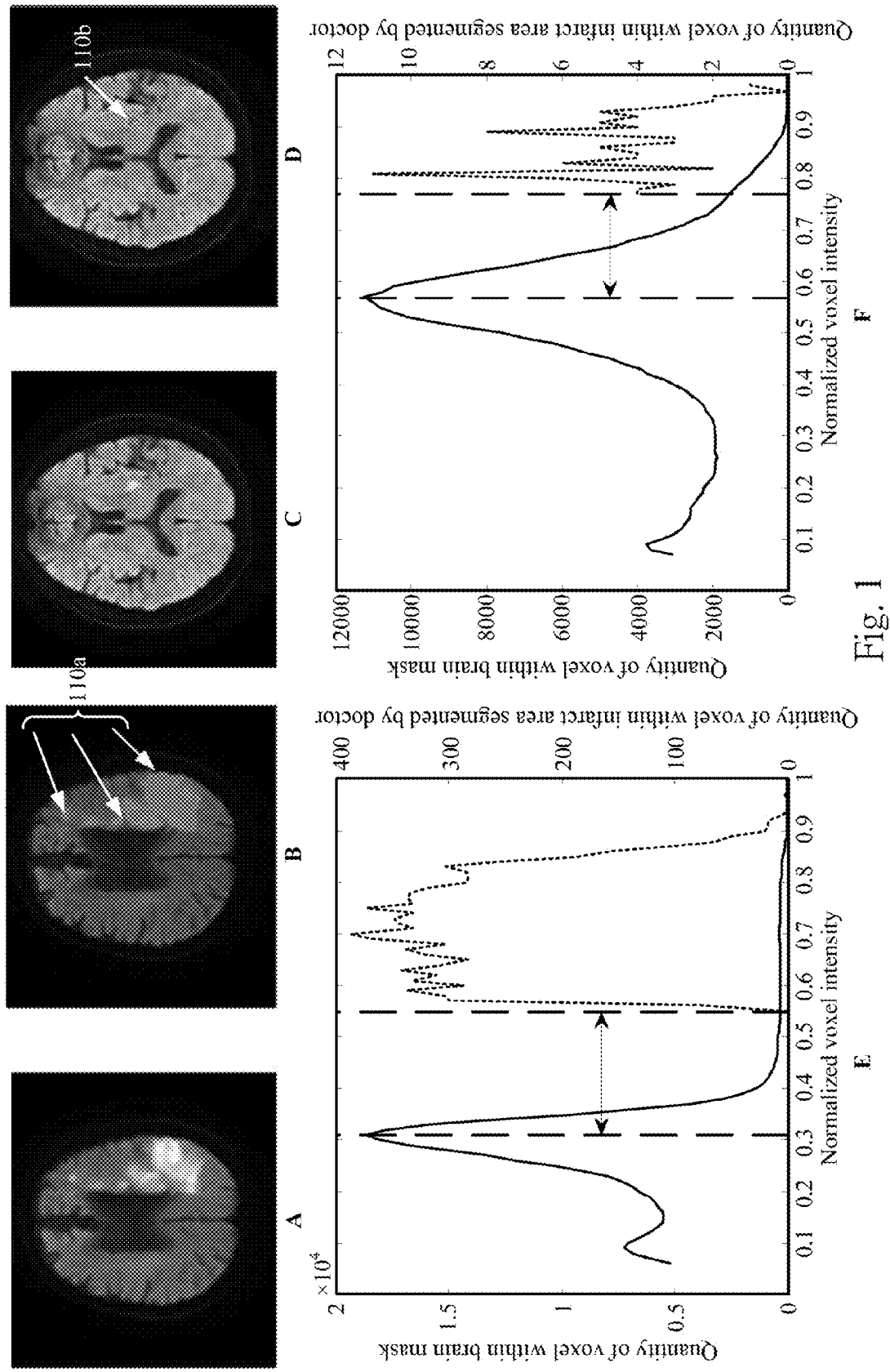
FIG. 1 illustrates diffusion-weighted imaging (DWI) images and normalized voxel intensity histograms of two subjects according to an embodiment of the present invention.

The detailed description provided below is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples. Therefore, the spirit and scope of the appended claims should not be limited to the description of the embodiments contained herein.

Currently, a semi-automatic segmentation method assisted by software is used in hospital to segment cerebral infarct. However, the semi-automatic segmentation method is time-consuming for processing and analyzing, and requires computer-assisted for specialist trained by additional image analysis to segment into normal brain tissue and cerebral infarct. It is prone to have variability between different raters, and thus the timing of using the semi-automatic segmentation method in clinical is constrained. The semi-automatic segmentation method cannot be used for assisting emergency physicians to benefit patients with acute stroke. The present invention provides methods for detecting and quantifying a cerebral infarct, which utilize a fuzzy C-means clustering and the characteristics of histograms of diffusion-weighted imaging (DWI) and apparent diffusion coefficient (ADC) map to develop a novel algorithm for cerebral infarct segmentation.

DWI images the rate of Brownian motion of water molecules by measuring the diffusion of the water molecules in the microstructure, which provides a better resolution than general magnetic resonance imaging (MRI) image. The principle of DWI is that by applying a bipolar gradient pulse to the microstructure, the signal of the water molecules starts to decay. The motionless water molecules in the cerebral infarct decays more slowly, and thus the signal of the cerebral infarct in DWI image is stronger. The principle of ADC map is similar to DWI, which indicates other factors that affects the flow direction of water molecules, and made into the ADC map according to signal-decaying degree at different gradient fields. Tissue with higher cell density has a weaker ADC signal. Cells in the cerebral infarct undergo cytotoxic edema due to hypoxia, which leads to narrow cell gap. The water molecules in the cerebral infarct has a slower rate of Brownian motion, and therefore the cerebral infarct has a stronger signal in DWI image and a weaker signal in ADC map. DWI image and ADC map can be used to diagnose cerebral infarct.

The method of the present invention applies fuzzy C-means (FCM) clustering, which is an unsupervised clustering method. The FCM clustering divides data with similar property into several clusters based on the distribution of the data, and analyzes the information of different clusters. The FCM clustering applies the concept of fuzzy clustering, which each of the data elements can belong to more than one cluster, and associated with each data element is a set of membership levels. In other words, each the data element does not belong to exactly one cluster. Instead, the FCM clustering indicates the strength of the association between the data element and a particular cluster by a number between 0-1.

A histogram shows the distribution of data. The present invention proposed that there is a difference value between the peak of the normalized DWI voxel intensity histogram, $I_{peak}$, which is the normalized DWI voxel intensity that most of the DWI voxels have, and the minimum normalized DWI voxel intensity of the cerebral infarct diagnosed by a neurologist using a semi-automatic segmentation method, and the difference value of every subjects are within a range. Therefore, the difference value can be used as a standard for separating cerebral infarct from normal brain tissue. It is noteworthy that the value can be adjusted according to different users and subjects, and thus calibration can be performed before using the method of the present invention to obtain the best detection result.

The image received from the MRI scanner in the method of the present invention has a thickness, and the method for quantifying a cerebral infarct of the present invention includes multiplying the area of the cerebral infarct detected by the method for detecting the cerebral infarct of the present invention by the slice thickness of the image to obtain the volume of the cerebral infarct.

The method of the present invention receives DWI image and ADC map from the MRI scanner, and executes subsequent calculating steps by computer programs and thereby achieve fast, accurate, and automatic detection and quantification of the cerebral infarct. The method of the present invention is benefit to doctors to diagnose and treat stroke patients in clinical.

Reference will now be made in detail to the present embodiments of the invention, examples of which are illustrated in the accompanying drawings. These are merely examples and are not intended to be limiting.

Embodiment

The images in Embodiment were received from a MRI scanner, which the model is Signa HDxt 1.5 T Optima Edition (GE Healthcare, Waukesha, Wis., US). The MRI scanner is equipped with a DWI scan and an ADC map ( ). The parameters of the DWI scan were set that TR/TE/Flip angle=6000 ms/82.8 ms/90°, field of view (FOV)=230 mm, matrix=128×128, in-plane resolution=1.79×1.79 mm, 24 axial slices, and 5 mm slice thickness with 1 mm gap. The parameter of the ADC map was set that b=1000 s/mm².

The steps of Embodiment were carried out with a MATLAB program (The MathWorks, Inc., Natick, Mass.), unless otherwise stated.

The method for detecting a cerebral infarct of an embodiment includes the following steps:

1. Co-registration and intensity normalization: The program used was Statistical Parametric Mapping 8 (SPM8, Wellcome Department of Cognitive Neurology, London, UK).
   a. 24 DWI images and 24 ADC maps of a subject were received form the MRI scanner, wherein each DWI image included a plurality of DWI voxels, each ADC map included a plurality of ADC voxels, and each DWI voxel had a DWI voxel intensity, each ADC voxel had an ADC voxel intensity.
   b. Because the DWI images and the ADC maps were captured at different times, the ADC maps were registered to the corresponding DWI images by a rigid registration, and calibrated by a trilinear interpolation to correct the differences due to head movements. The rigid registration includes translation and rotation, and can compare and fuse images of the same object obtained under different conditions thereby achieve the purpose of information fusion. Trilinear interpolation is a method of multivariate interpolation on a 3-dimensional regular grid, which is frequently used in image enlargement and image rotation.
2. A brain mask of the subject in the DWI image was determined, and the DWI voxels inside the brain mask were selected for subsequent steps. The software used was Brain Extraction Tool (BET, FMRIB Centre, University of Oxford, Oxford, UK) to identify the inner and the outer surface of the skull of the subject. The fractional intensity threshold was sat at 0.3 in Embodiment, which is smaller than the default value 0.5, to obtain a larger estimated brain outline, and thus not eliminate any possible cerebral infarct region. The purpose of this step is to eliminate the voxels of non-brain tissue, which is the background, in the DWI images to benefit the subsequent detection and quantification of the cerebral infarct.
3. The DWI voxel intensities and the ADC voxel intensities of the voxels within the brain mask were normalized to make the DWI voxel intensities and the ADC voxel intensities disperse in a standard range (0, 1), and a normalized DWI voxel intensity histogram and a normalized ADC voxel intensity histogram were formed.
4. Pre-screening:
   a. The normalized DWI voxel intensity histogram was filtered by a wave filter. The smoothed normalized DWI voxel intensity histogram had a peak, $I_{peak}$. The wave filter used in the embodiment was a third-order moving-average filter. The purpose of this step was to smooth the histogram.
   b. The DWI voxels having normalized DWI voxel intensity smaller than or equal to the $I_{peak}$ were unlikely to be the cerebral infarct, and were eliminated to enhance the efficiency of fuzzy C-means clustering, and to reduce the amount of computation in the following steps, which can improve the accuracy of detection.
5. The DWI voxels after the pre-screening were clustered by an unsupervised FCM clustering to form 50 DWI voxel clusters, wherein each of the DWI voxel clusters had a first average normalized DWI voxel intensity.
6. Forming candidate DWI voxel cluster:
   a. A threshold was determined, which was the $I_{peak}$+ a value, and the value is a difference value between a minimum normalized voxel intensity of the cerebral infarct diagnosed by a semi-automatic segmentation method and the $I_{peak}$.
   b. The DWI voxel cluster having the first average normalized DWI voxel intensity larger than the threshold was selected to form the candidate DWI voxel cluster.
7. Eliminating voxel labels with insufficient intensity:
   a. The candidate DWI voxel cluster was further divided into at least one DWI voxel label, which was based on the location of the voxel label. Each of the DWI voxel labels had a second average normalized DWI voxel intensity.
   b. The DWI voxel label having the second average normalized DWI voxel intensity larger than the threshold was selected. Because not every individual DWI voxels belonging to the candidate DWI voxel cluster formed in the detecting step 6 had voxel intensity larger than the threshold, further dividing was needed to eliminate the voxels with insufficient intensity.
8. An edge of each DWI voxel label was determined to eliminate the DWI voxel label with weak edge. The edge map was extracted from normalized DWI by using Canny edge detector. The low and high thresholds were set as (0, 0.3), and the parameter of the standard deviation of the Gaussian filter was set as 1. Usually, the cerebral infarct has an obvious edge, and thus this step can eliminate normal brain tissue misdiagnosed as cerebral infarct due to higher DWI voxel intensity to prevent false positives.
9. Eliminating DWI voxel labels selected due to magnetic inhomogeneity:
   a. A peak of the normalized ADC voxel intensity histogram and an average normalized ADC voxel intensity of lower half voxel intensities of the ADC voxels corresponding to the DWI voxel label were determined, and were represented by $I_{peak,\ ADC}$ and $I_{lower\ mean,\ ADC}$, respectively.

b. The DWI voxel label with $I_{lower\ mean,\ ADC}/I_{peak,\ ADC} \geq 0.5$ was considered as an artifact caused by magnetic inhomogeneity and was eliminated. The artifact may be caused by the magnetic susceptibility differences between adjacent air and cerebrospinal fluid structures, or by the surrounding soft tissues with echo-planar imaging techniques. The signal intensities of the magnetic inhomogeneity created artifact are commensurate with those of the cerebral infarct, and it is difficult to distinguish between the two. However, in the ADC map, the signal intensities of the cerebral infarct are weak, and are weaker than those of the artifact. This property was used in this step to detect and eliminate the artifacts that were difficult to distinguish in the DWI images.

The sum of the candidate DWI voxel labels in each DWI images were the cerebral infarct in the brain of the subject, which the candidate DWI voxel labels were the DWI voxel labels screened by the foregoing steps, wherein the detecting steps 8 and 9 can be optionally carried out depending on the DWI images of the subject.

The method for quantifying the cerebral infarct of an embodiment includes the following steps:

1. The cerebral infarct was determined by the aforementioned 9-step method for detecting the cerebral infarct.
2. The volume of the cerebral infarct was the sum of the area of the cerebral infarct detected in each DWI image multiplying by the slice thickness of the DWI image. In one embodiment, the slice thickness of the DWI image was 5 mm.

Comparative Example

Comparative example utilized the traditional semi-automatic segmentation method by a specialist (neurologist) to diagnose the volume of the cerebral infarct of 22 subjects. The cerebral infarct was judged artificially based on the images from the MRI scanner.

The date of the subjects of Embodiment are shown in the following Table 1, including the gender, age, infarct volume detected by Comparative example (semi-automatic segmentation method), infarct volume detected by Embodiment (automatic segmentation method), and relevance between Comparative example and Embodiment. It is noteworthy that the detecting and quantifying method of Embodiment were conducted on the subjects for 10 times, and Table 1 shows the average of the 10 results.

In order to judge the relevance between Comparative example and Embodiment and the accuracy of Embodiment, the neurologist gave each subject four parameters based on the diagnosis by Embodiment and Comparative example, including true positive (TP), true negative (TN), false positive (FP), and false negative (FN).

Similarity index (SI) was used in the present invention to judge the relevance between the cerebral infarcts detected by Comparative example and Embodiment, and sensitivity, specificity, positive predictive value (PPV), and negative predictive value (NPV) were used in the present invention to judge the accuracy of the cerebral infarct detected by Embodiment.

The meanings of each index in Table 1 were as following:
SI: The relevance between the results diagnosed by the method of Embodiment and by the neurologist (Comparative example).
Sensitivity: The percentage of sick people who are correctly identified as positive.
Specificity: The percentage of healthy people who are correctly identified as negative.
PPV: The percentage of all positive results that are true positive results.
NPV: The percentage of all negative results that are true negative results.

TABLE 1

| | | | | Infarct volume (mL) | | | | | | |
|---|---|---|---|---|---|---|---|---|---|---|
| Subject | Gender | Age | Value | Comparative example | Embodiment | ΔVolume[1] (%) | SI[2] (%) | Sensitivity (%) | Specificity (%) | PPV (%) | NPV (%) |
| 1 | M | 73 | 0.27 | 0.155 | 0.212 | 36.6 | 84.661 | 100.000 | 99.999 | 73.529 | 100.000 |
| 2 | M | 80 | 0.19 | 0.358 | 0.377 | 5.3 | 97.438 | 100.000 | 100.000 | 95.014 | 100.000 |
| 3 | F | 69 | 0.21 | 0.399 | 0.381 | -4.4 | 97.716 | 95.556 | 100.000 | 100.000 | 100.000 |
| 4 | F | 84 | 0.22 | 0.474 | 0.378 | -20.3 | 86.835 | 78.037 | 100.000 | 98.349 | 99.998 |
| 5 | F | 70 | 0.2 | 0.501 | 0.337 | -32.7 | 91.662 | 93.398 | 100.000 | 91.723 | 100.000 |
| 6 | M | 63 | 0.19 | 0.545 | 0.451 | -17.2 | 90.413 | 82.764 | 100.000 | 100.000 | 99.999 |
| 7 | M | 55 | 0.2 | 0.612 | 0.471 | -22.9 | 82.684 | 73.190 | 100.000 | 95.072 | 99.998 |
| 8 | F | 66 | 0.15 | 0.644 | 0.479 | -25.6 | 85.332 | 74.436 | 100.000 | 100.000 | 99.998 |
| 9 | M | 61 | 0.21 | 0.796 | 0.895 | 12.5 | 94.143 | 100.000 | 99.999 | 88.938 | 100.000 |
| 10 | M | 64 | 0.19 | 1.003 | 1.019 | 1.6 | 98.927 | 99.710 | 100.000 | 98.171 | 100.000 |
| 11 | F | 75 | 0.25 | 1.675 | 1.794 | 7.1 | 94.373 | 97.619 | 99.998 | 91.568 | 99.999 |
| 12 | F | 56 | 0.19 | 1.966 | 1.497 | -23.9 | 86.438 | 76.140 | 100.000 | 100.000 | 99.992 |
| 13 | F | 74 | 0.31 | 2.141 | 3.232 | 51.0 | 79.722 | 100.000 | 99.984 | 66.312 | 100.000 |
| 14 | F | 86 | 0.14 | 3.749 | 2.228 | -40.6 | 74.359 | 59.444 | 100.000 | 100.000 | 99.977 |
| 15 | M | 76 | 0.19 | 4.143 | 3.448 | -16.8 | 85.827 | 78.898 | 99.997 | 95.789 | 99.987 |
| 16 | F | 87 | 0.17 | 10.108 | 8.351 | -17.4 | 90.453 | 82.621 | 100.000 | 100.000 | 99.975 |
| 17 | F | 83 | 0.16 | 12.657 | 10.088 | -20.3 | 88.603 | 79.662 | 100.000 | 99.952 | 99.958 |
| 18 | F | 57 | 0.19 | 13.063 | 13.492 | 3.3 | 97.656 | 99.254 | 99.992 | 96.124 | 99.999 |
| 19 | M | 72 | 0.19 | 15.014 | 11.611 | -22.7 | 87.181 | 77.332 | 100.000 | 99.992 | 99.955 |
| 20 | M | 80 | 0.24 | 46.828 | 54.497 | 16.4 | 92.426 | 99.990 | 99.894 | 85.933 | 100.000 |
| 21 | M | 74 | 0.22 | 56.517 | 59.147 | 4.7 | 97.526 | 99.793 | 99.956 | 95.365 | 99.998 |
| 22 | M | 91 | 0.1 | 482.939 | 429.534 | -11.1 | 94.147 | 88.942 | 100.000 | 100.000 | 99.056 |
| Average | | 72.5 | 0.20 | | | -6.2 | 89.933 | 88.036 | 99.992 | 94.174 | 99.949 |
| SD[3] | | 10.4 | 0.04 | | | 22.3 | 6.460 | 12.117 | 0.024 | 8.886 | 0.200 |

[1] ΔVolume (%) = (Volume detected by Comparative example − Volume detected by Embodiment)/Volume detected by Comparative example × 100%
[2] SI (%) = 2 × TP/(2 × TP + FP + FN) × 100%
[3] SD = Standard deviation According to the results of the 22 subjects in Table 1, the value was between 0.1-0.31, and the average of the value of the 22 subjects was 0.2. Moreover, as the ΔVolume, SI, sensitivity, specificity, PPV, and NPV shown in Table 1, the automatic segmentation method of the present embodiment has good accuracy and a high relevance to the semi-automatic segmentation method of Comparative example.

It is noteworthy that the threshold of subject No. 13 was set at $I_{peak}+0.31$, which the value was higher than the average, representing that less region was detected as cerebral infarct, and thus has poor SI (79.722%) comparing to other subjects. On the other hand, the threshold of subject No. 14 was set at $I_{peak}+0.14$, which the value was lower than the average, representing that more region was detected as cerebral infarct, and thus has poor SI (74.359%) and sensitivity (59.444%) comparing to other subjects. The purpose is to demonstrate that the semi-automatic segmentation method currently used in hospitals couldn't accurately diagnose the cerebral infarct due to the inconsistency of artificial judgment by a neurologist.

FIG. 1 shows images of two subjects in Embodiment of the present invention. Parts A and C are DWI images of subject No. 20 and subject No. 3 respectively. Parts B and D are marked DWI images of subject No. 20 and subject No. 3 respectively, which the marked regions (indicated by arrows 110a and 110b respectively in Parts B and D) in the DWI images were the cerebral infarct diagnosed by the neurologist. Parts E and F are normalized DWI voxel intensity histograms of subject No. 20 and subject No. 3 respectively, which the solid lines refer to the left vertical axes, and the dotted lines refer to the right vertical axes. As shown in Parts E and F, the value of subject No. 20 was 0.24, and the value of subject No. 3 was 0.21. FIG. 1 illustrates one example with a large cerebral infarct area and another with a small cerebral infarct area.

Figure 2:
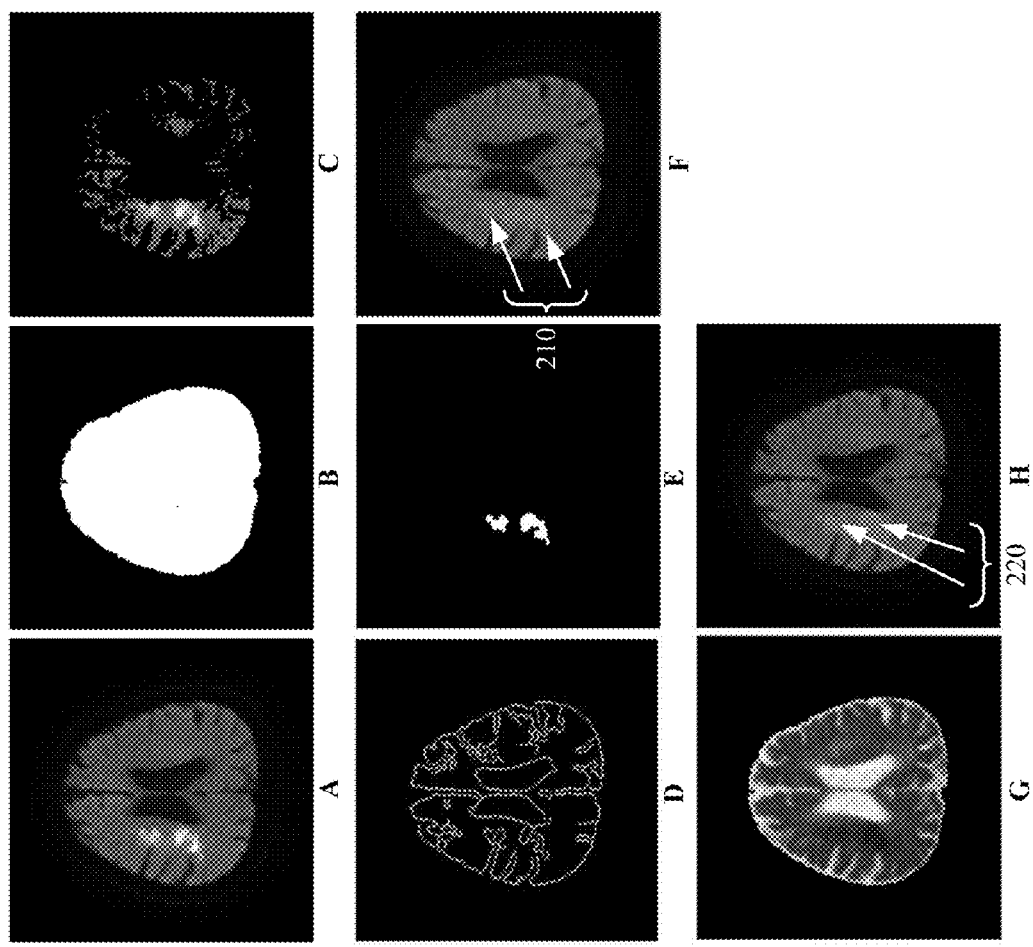
FIG. 2 illustrates images at various steps according to an embodiment of the present invention.

FIG. 2 illustrates images at various steps of Embodiment, which uses the images of subject No. 9 at each detecting steps as an exemplary description. Part A shows an original DWI image received from the MRI scanner. Part B shows the brain mask determined in the detecting step 2. Part C shows the voxels after the pre-screening in the detecting step 4. Part D shows the Canny edge detection map determined in the detecting step 8. Part E shows the cerebral infarct detected by Embodiment of the present invention. Part F shows the marked DWI image that the cerebral infarct detected by Embodiment was marked on the original DWI image and indicated by arrows 210. Part G shows the ADC map. Part H shows the cerebral infarct diagnosed by the neurologist using the semi-automatic segmentation method and marked on the original DWI image, which is indicated by arrows 220. It is noteworthy that judging by this DWI image of subject No. 9, the detecting steps 8 and 9 were not carried out, and thus the cerebral infarct shown in Part E of FIG. 2 was determined by the detecting steps 1-7.

Figure 3:
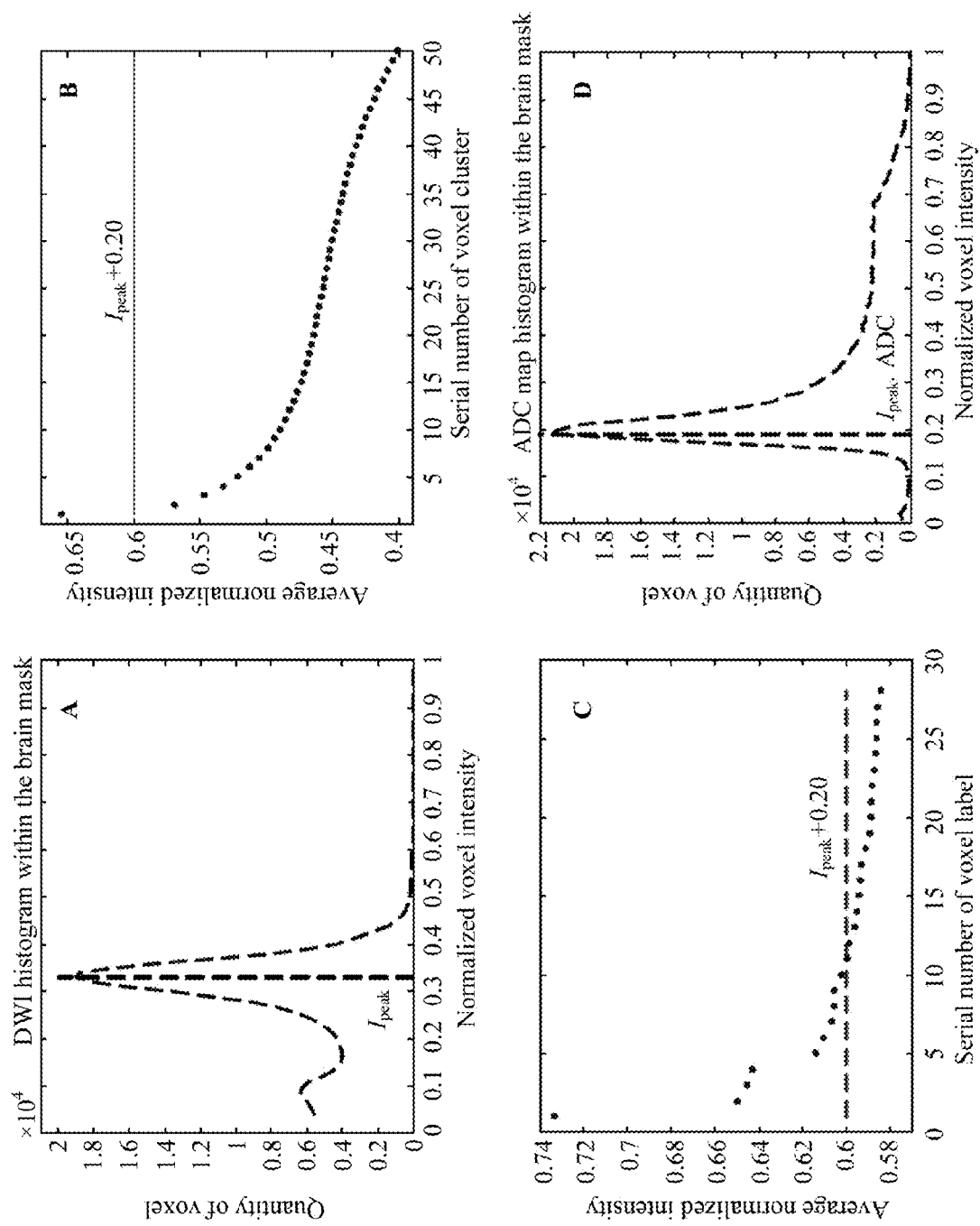
FIG. 3 illustrates histograms and distribution graphs utilized at various steps according to an embodiment of the present invention.

FIG. 3 illustrates histograms and distribution graphs utilized at various steps of Embodiment of the present invention, which uses the voxel intensity histograms and average voxel intensity distribution graphs of subject No. 9 to explain the screening manner in the detecting method of Embodiment. Part A is the normalized DWI voxel intensity histogram within the brain mask and after being filtered. The histogram has a peak, $I_{peak}$, and the DWI voxels having normalized DWI voxel intensity smaller than or equal to the $I_{peak}$ were eliminated in the detecting step 4. Part B is the average normalized voxel intensity distribution graph of voxel clusters, which shows the first average normalized DWI voxel intensity of the 50 DWI voxel clusters after the FCM clustering in the detecting step 5, and are arranged in descending order. Only voxel cluster No. 1 was considered as candidate DWI voxel cluster in accordance to the detecting step 6. Part C is the average normalized voxel intensity distribution graph of voxel labels, which shows the second average normalized DWI voxel intensity of the 28 voxel labels divided from the voxel cluster No. 1 in accordance to the detecting step 7, and are arranged in descending order. The DWI voxel labels having the second average normalized DWI voxel intensity smaller than or equal to the $I_{peak}+0.2$ were eliminated. Part D is the normalized ADC voxel intensity histogram, which was used in the detecting step 9 to distinguish the artifacts due to magnetic inhomogeneity.

Figure 4:
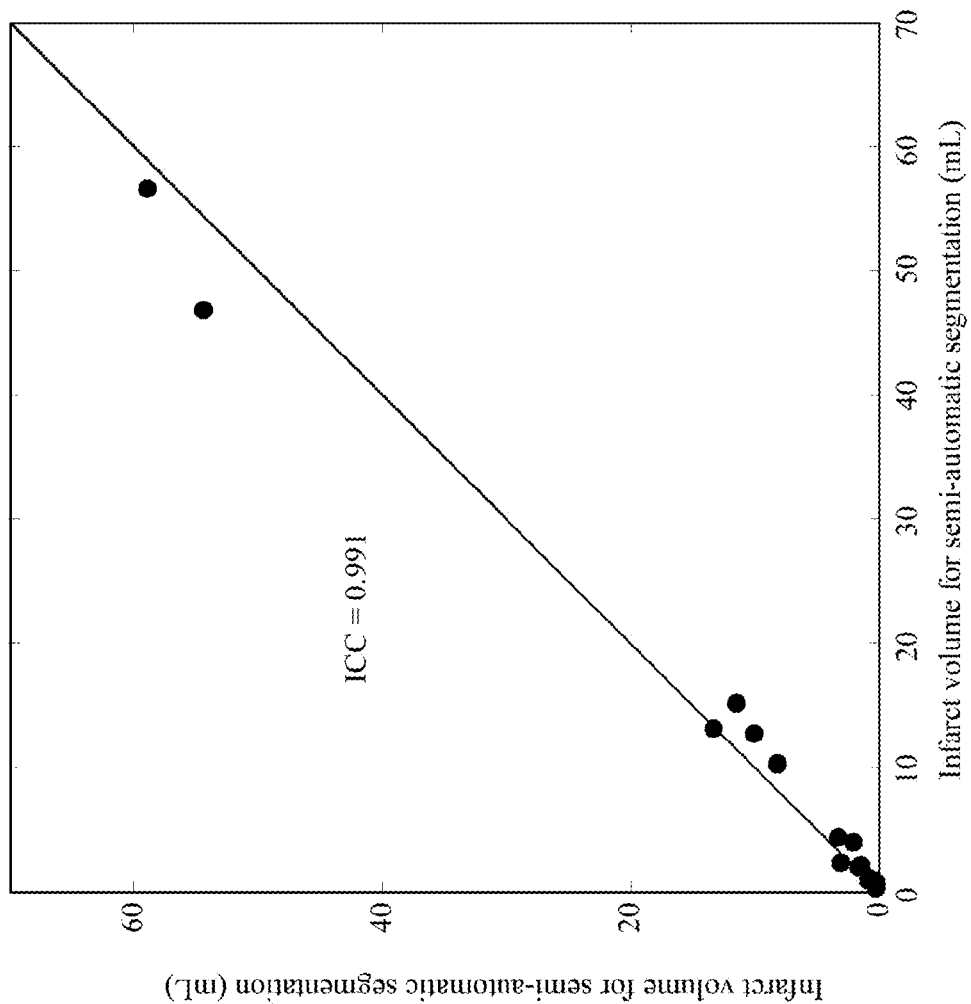
FIG. 4 illustrates a diagram of the detecting results between an embodiment of the present invention and a comparative example.

FIG. 4 illustrates a diagram of the detecting results between Embodiment of the present invention and Comparative example to compare the total cerebral infarct volume diagnosed by the automatic segmentation method of Embodiment with the total cerebral infarct volume diagnosed by the semi-automatic segmentation method used in Comparative example. The intraclass correlation coefficient (ICC) was used to evaluate the relevance between Embodiment and Comparative example. As shown in FIG. 4, there was a good relevance between Embodiment and Comparative example, and the ICC was 0.991. It is noteworthy that the total cerebral infarct of subject No. 22 was much larger than other subjects, which was an outlier, and thus the data of subject No. 22 was not included in FIG. 4 and the ICC. The ICC with the data of subject No. 22 would be 0.993. The ICC is one of the indicators to assess the reliability coefficient between two or more groups, and the reliability coefficient represents consistency, stability, and reliability of measurement results. The value of the ICC is between 0 to 1, which 0 represents not reliable, and 1 represents completely reliable. In general, having an ICC below 0.4 is regarded as poor reliability, and having an ICC above 0.75 is regarded as good reliability.

Figure 5:
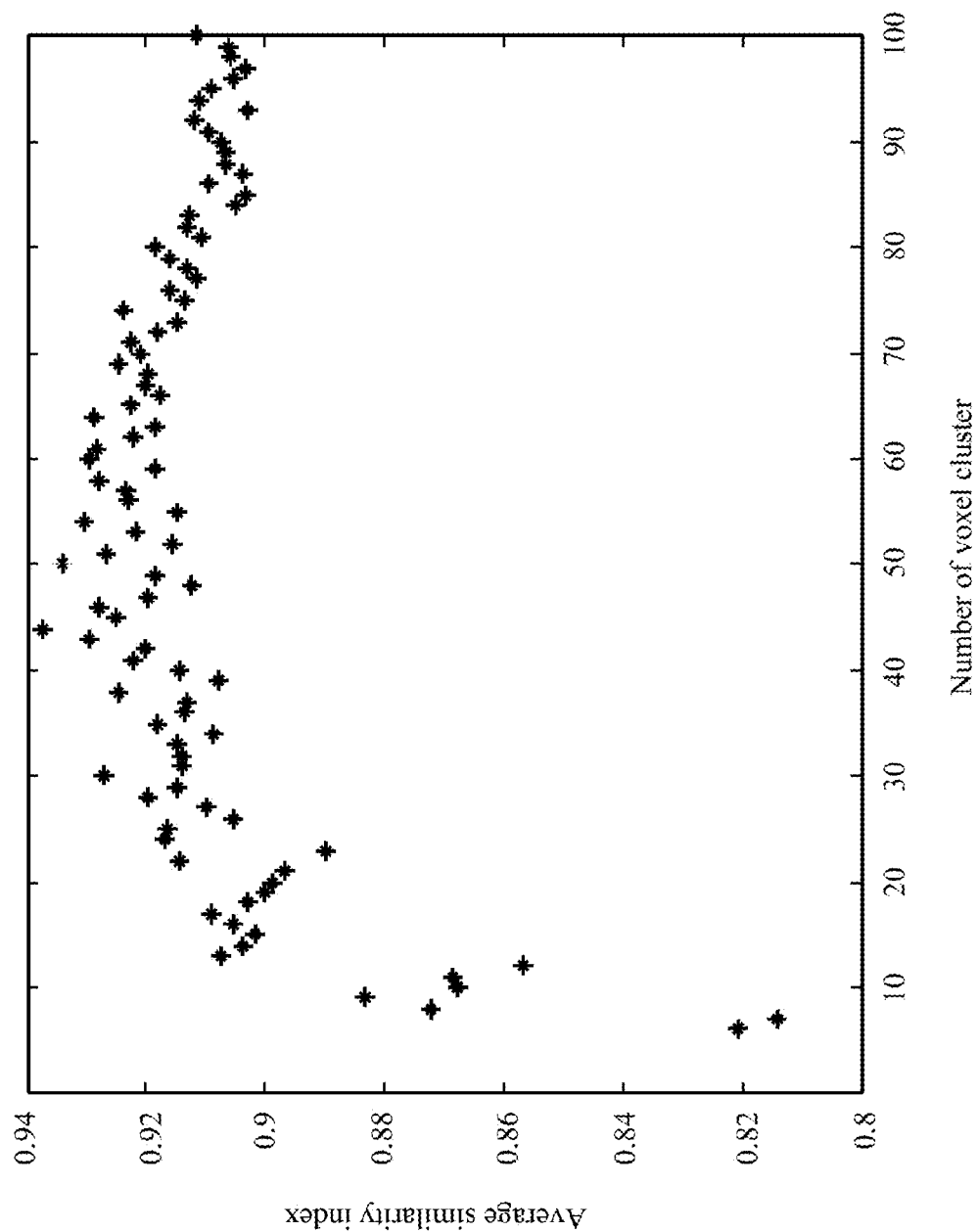
FIG. 5 illustrates an average similarity index (SI) versus the number of fuzzy C-mean (FCM) clustering diagram according to an embodiment of the present invention.

FIG. 5 illustrates an average similarity index (SI) versus the number of FCM clustering diagram according to an embodiment of the present invention. As shown in FIG. 5, the number of FCM clustering is related to the SI. According to one embodiment of the present invention, the voxel clusters includes 6-100 voxel clusters. Preferably, when the voxel clusters includes 50 voxel clusters, the better SI is obtained. It is noteworthy that the SI was calculated by the voxel label selected by the detecting steps 1-7.

Figure 6:
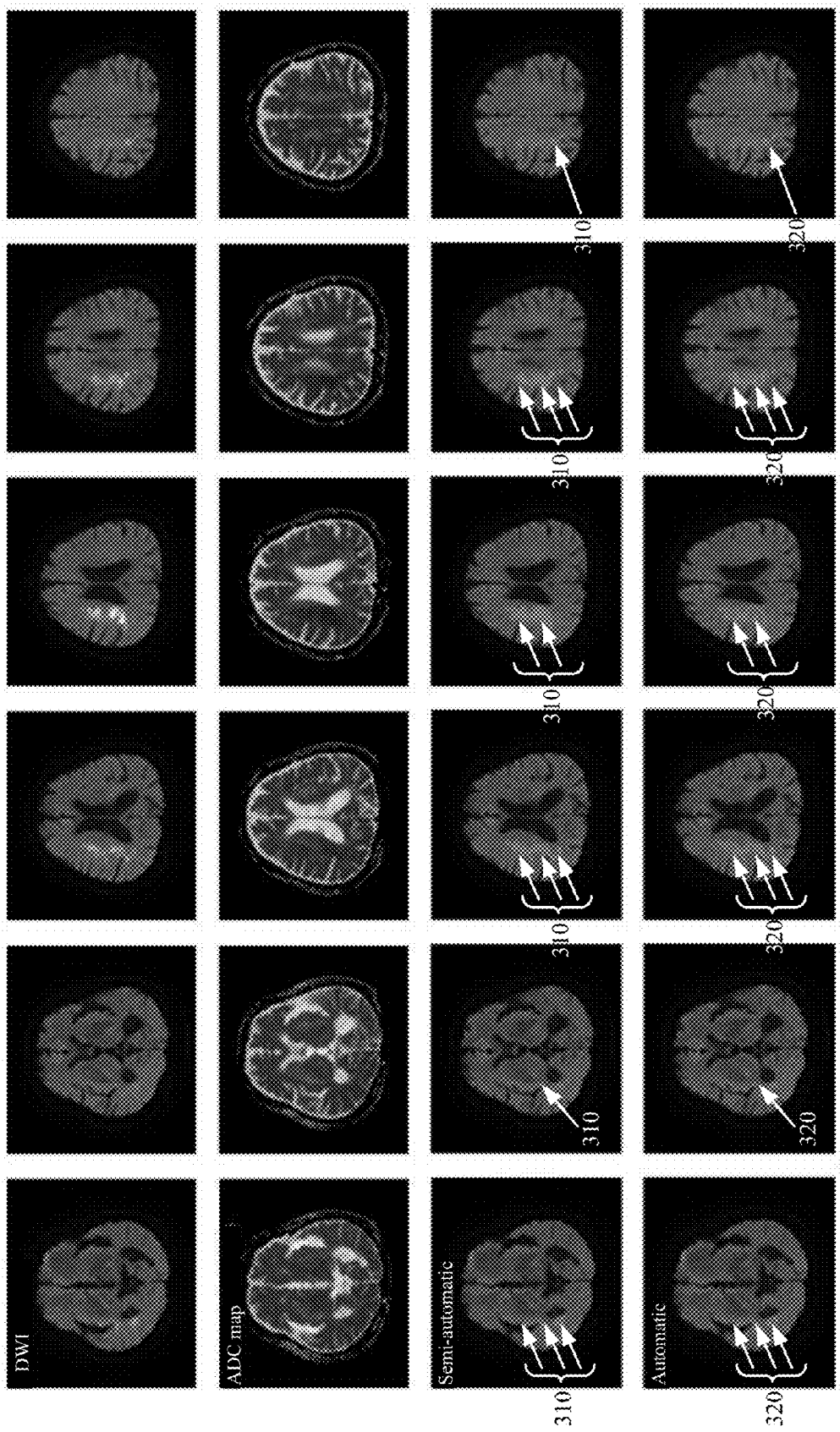
FIG. 6 illustrates DWI images, apparent diffusion coefficient (ADC) maps, and detecting results of a comparative example and an embodiment of the present invention of a subject.

FIG. 6 shows a portion of images of subject No. 9, which rows 1 to 4 are DWI images, ADC maps, detecting results of Comparative example, i.e. the semi-automatic segmentation method used by the neurologist, and detecting results of Embodiment, i.e. the automatic segmentation method of the present invention, respectively. FIG. 6 is to compare the cerebral infarct diagnosed by the semi-automatic segmentation method (indicate by arrows 310) with the cerebral infarct diagnosed by the automatic segmentation method (indicate by arrows 320), and the results show that the cerebral infarcts diagnosed by Embodiment and Comparative example have good similarity.

Figure 7:
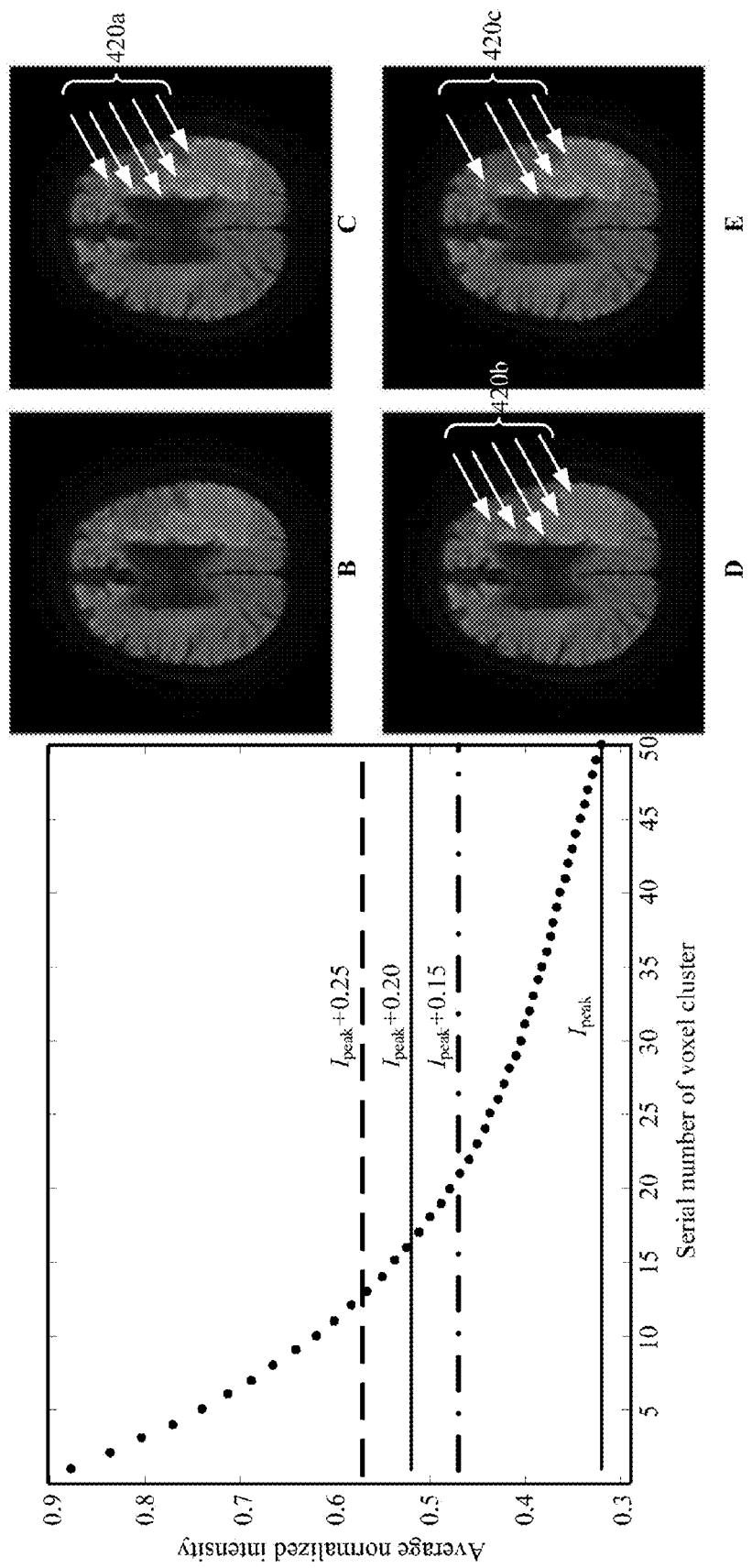
FIG. 7 illustrates an average normalized voxel intensity distribution graph and detecting result images with different thresholds of a subject in an embodiment of the present invention.

FIG. 7 shows an average normalized voxel intensity distribution graph and detecting result images with different thresholds of a subject detected by Embodiment. FIG. 7 is to discuss the relationship between the threshold and the detected cerebral infarct. Part A is the average normalized voxel intensity distribution graph of the voxel clusters of the subject, and the threshold was set at $I_{peak}+0.15$, $I_{peak}+0.2$, and $I_{peak}+0.25$, which the detected cerebral infarcts were marked in the images shown in Parts C, D, and E and indicated by arrows 420a, 420b, and 420c, respectively. Part B is the original DWI image. When the threshold was set at $I_{peak}+$ 0.15, $I_{peak}$+0.2, and $I_{peak}$+0.25, the SI was 88.4%, 93.3%, and 99.2%, respectively, and the sensitivity was 100.0%, 99.9%, and 98.4%, respectively. Therefore, when the threshold is set at $I_{peak}$+0.2, the method of the present invention has both better SI and sensitivity.

Figure 8:
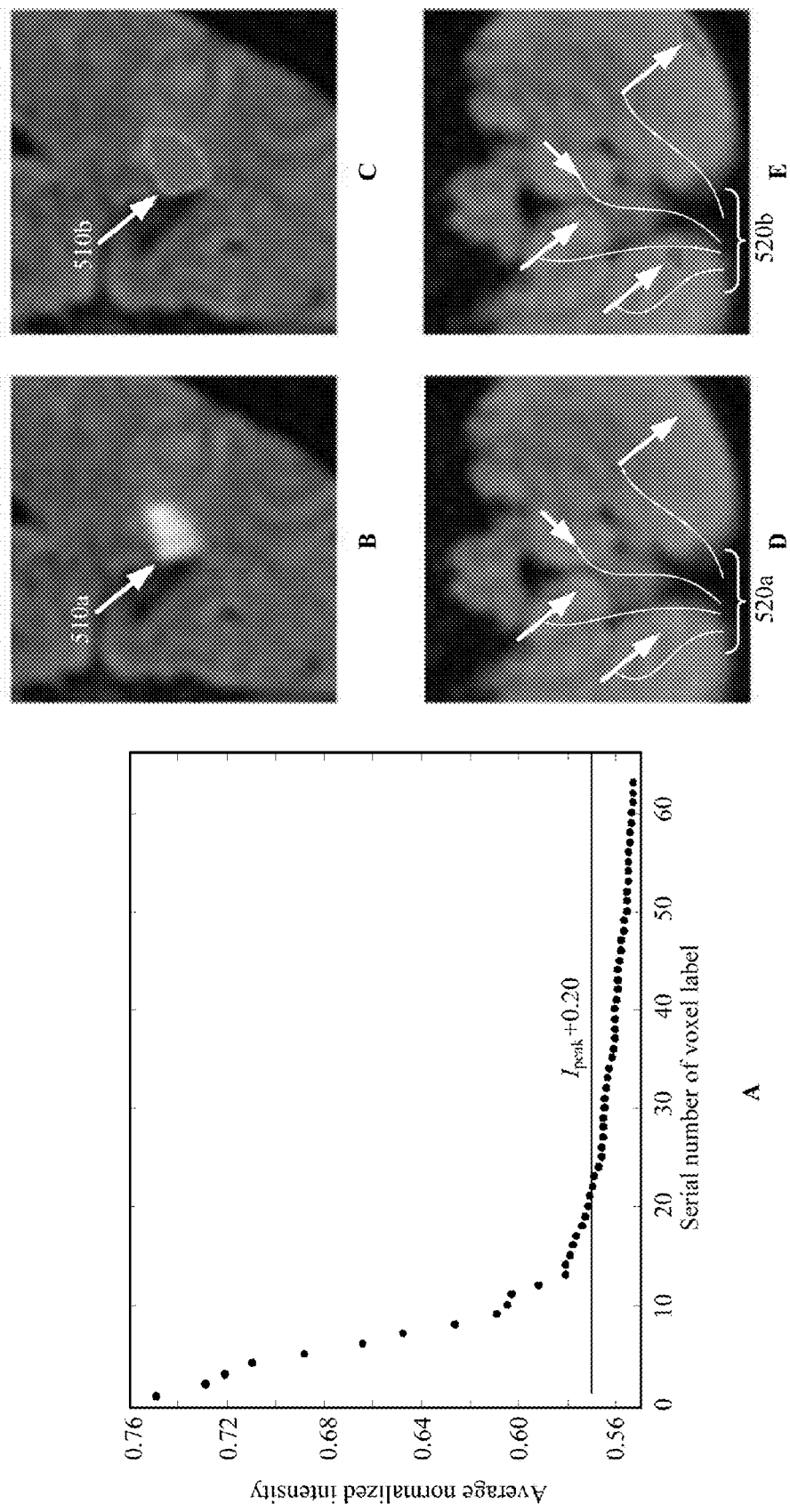
FIG. 8 illustrates an operational diagram at one step according to an embodiment of the present invention.

FIG. 8 illustrates an operational diagram at one step according to an embodiment of the present invention, which applies images of a subject in Embodiment to describe the operation of eliminating voxel labels with insufficient intensity in the detecting step 7. In this step, the candidate DWI voxel clusters formed in the detecting step 6 were further divided into 63 voxel labels. Part A shows the second average normalized voxel intensity distribution graph arranged in descending order, and the threshold was set at $I_{peak}$+0.2. Part B shows a voxel label that was true positive (indicated by an arrow 510a), which the second average normalized voxel intensity of the voxel label was larger than the threshold, and the voxel label had strong signal in the DWI image. The voxel label in Part B was regarded as cerebral infarct, and marked in the original DWI image as shown in Part C. The marked region is indicated by an arrow 510b. Par D shows four voxel labels that were false positive (indicated by arrows 520a), which the second average normalized voxel intensities of the voxel labels were smaller than the threshold, and the voxel labels had weak signals in the DWI image. The voxel labels in Part D were not regarded as cerebral infarcts, and marked in the original DWI image as shown in Part E. The marked regions are indicated by arrows 520b.

Figure 9:
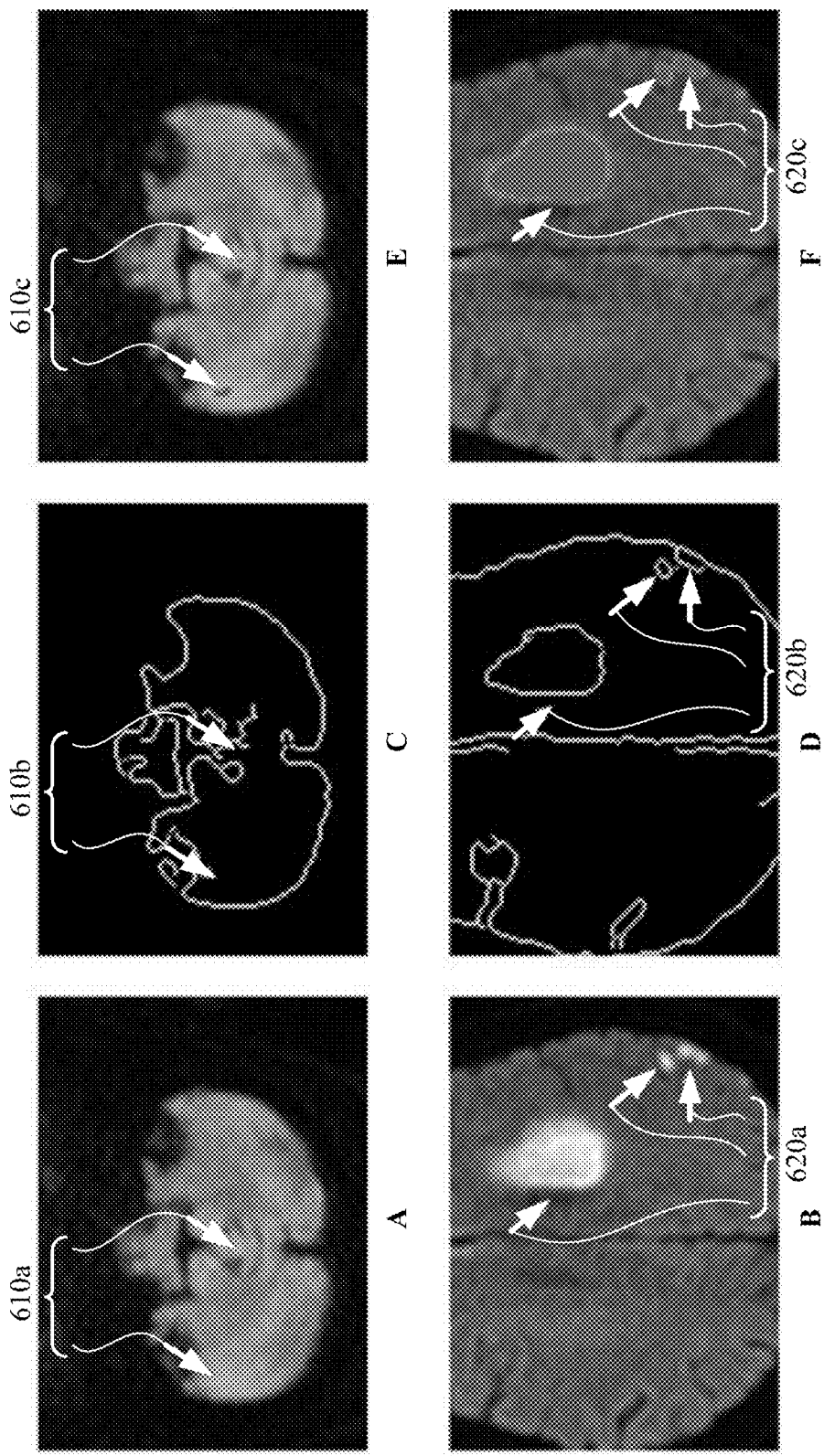
FIG. 9 illustrates an operational diagram at another step according to an embodiment of the present invention.

FIG. 9 illustrates an operational diagram at another step according to an embodiment of the present invention, which applies images of a subject in Embodiment to describe the operation of eliminating voxel labels with weak edge in the detecting step 8. Parts A and B show the voxel labels selected in the detecting step 7, and the voxel labels were respectively indicated by arrows 610a and 620a in the DWI images. Part C is the Canny edge map extracted from Part A. The voxel labels indicated by the arrows 610a in Part A did not have corresponding edges in Part C (indicated by arrows 610b). Therefore, the voxel labels were not regarded as cerebral infarct, and were marked in the original DWI image as shown in Part E. The marked regions are indicated by arrows 610c. Part D is the Canny edge map extracted from Part B. The voxel labels indicated by the arrows 620a in Part B had corresponding edges in Part D (indicated by arrows 620b). Therefore, the voxel labels were regarded as cerebral infarcts, and were marked in the original DWI image as shown in Part F. The marked regions are indicated by arrows 620c.

Figure 10:
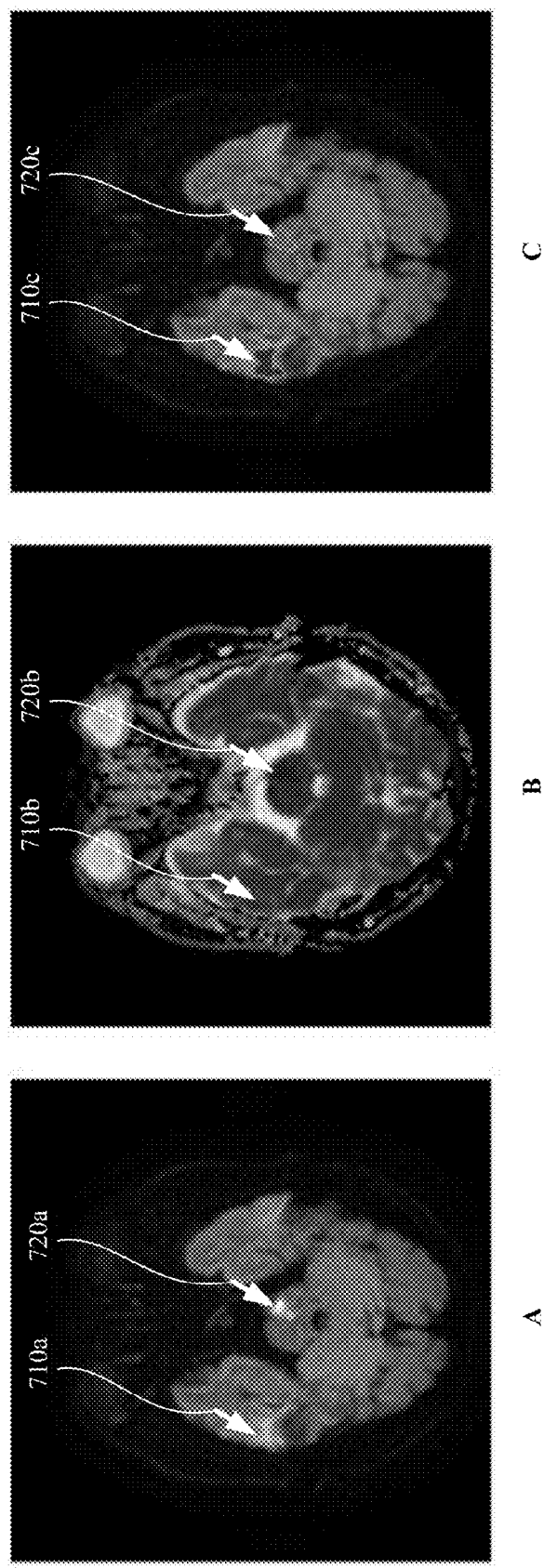
FIG. 10 illustrates an operational diagram at yet another step according to an embodiment of the present invention.

FIG. 10 illustrates an operational diagram at yet another step according to an embodiment of the present invention, which applies images of a subject in Embodiment to describe the operation of eliminating voxel labels selected due to magnetic inhomogeneity in the detecting step 9. Part A is a DWI image of the subject, showing two voxel labels with equivalent DWI voxel intensities, which are indicated by arrows 710a and 720a. Part B is an ADC map of the subject, and the two voxel labels in Part A are indicated by arrows 710b and 720b at corresponding positions in Part B. The two voxel labels in the ADC map have different ADC voxel densities. The cerebral infarct has a weaker signal than that of non-infarct region in ADC map. The voxel label indicated by the arrow 720b has a weaker signal than that of the voxel label indicated by the arrow 710b as shown in Part B. The two voxel labels were marked in the original DWI image as shown in Part C. As shown in Part C, the cerebral infarct (indicated by an arrow 720c) is distinguished from the artifact (indicated by an arrow 710c) created by magnetic inhomogeneity based on the ADC voxel intensities. The method of the present invention applies the ADC map to eliminate artifacts created by magnetic and thereby improves the accuracy for detecting the cerebral infarct and the similarity index with the result diagnosed by a doctor.

The method of the present invention can be accomplished in few minutes. It takes about 5 minutes to thoroughly perform the detecting steps 1 to 8 of Embodiment. If the functions of the program, SPM8, used in the detecting step 1 and the software, BET, used in the detecting step 2 are incorporated into the MATLAB program, the detecting speed of the method can be accelerated, which may be accomplished in 90 seconds.

Comparing to automatic segmentation method proposed in the past, the method of the present invention can detect the cerebral infarct more accurately, and has better similarity index with the semi-automatic segmentation method used by doctors. The average SI in Embodiment was 89.933%. The key to the abovementioned characteristics includes:

1. Performing pre-screening before FCM clustering: This step eliminates the voxels with voxel intensity smaller than or equal to the $I_{peak}$ to improve the efficiency of FCM clustering, and reduce the amount of computation in the following steps, which can improve the accuracy of detection.
2. The number of FCU clustering: As shown in FIG. 5, the number of FCM clustering may affect the SI.
3. Threshold: As shown in FIG. 7, using different thresholds as a criterion may affect the final SI. A suitable threshold may be obtained by statistical analysis on a training set, making the proposed algorithm adoptable to all situations.
4. Eliminating false-positive voxel labels in the candidate voxel clusters: The candidate voxel clusters before adopting the detecting step 7 may include false-positive infarct regions. Therefore, by further dividing into voxel labels based on the location in the detecting step 7, the voxel labels with low voxel intensity can be eliminated, that the false positives could mostly become true negatives, as shown in FIG. 8.
5. Eliminating voxel labels with weak edge: The result of the detecting step 7 may still contain false-positive voxel labels, that there are non-infarct regions with sufficient voxel intensities to pass the screening in the detecting steps 6 and 7. Because the false-positive voxel labels usually have weaker edges than the cerebral infarct, the detecting step 8 utilizes this characteristic to eliminate the false-positive voxel labels, as shown in FIG. 9.
6. Eliminating artifacts caused by magnetic inhomogeneity: The result of the detecting step 8 may still contain false-positive voxel labels, which are artifacts magnetic inhomogeneity. In the detecting step 9, the artifacts that are difficult to distinguish in the DWI images may be eliminated by cooperating with the ADC maps, as shown in FIG. 10.

The methods for detecting and quantifying the cerebral infarct of the present invention utilize the FCM clustering and the characteristics of histograms of DWI image and the ADC map, and have high SI. The methods of the present invention are rapid, real-time, and accurate methods for detecting and quantifying the cerebral infarct of stroke patients.

It will be apparent to those ordinarily skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A method for detecting a cerebral infarct, comprising:
receiving an image of a brain of a subject from a magnetic resonance imaging scanner, wherein the image has a plurality of voxels, and each of the voxels has a voxel intensity;
normalizing the voxel intensities to make the voxel intensities disperse in a standard range, wherein the normalized voxel intensities have a distribution peak, and the normalized voxel intensity of the distribution peak is $I_{peak}$;
determining a threshold, which is the $I_{peak}$+ a value, wherein the value is a difference value between a minimum normalized voxel intensity of the cerebral infarct diagnosed by a semi-automatic segmentation method and the $I_{peak}$; and
selecting voxel having the normalized voxel intensity larger than the threshold, wherein the selected voxel is the cerebral infarct.

2. The method of claim 1, wherein receiving the image of the brain of the subject from the magnetic resonance imaging scanner comprises determining a brain mask of the subject in the image.

3. The method of claim 2 wherein the brain mask comprises an inner surface and an outer surface of a skull of the subject.

4. The method of claim 1, wherein the image is obtained by diffusion-weighted imaging (DWI).

5. The method of claim 1, wherein the standard range is (0, 1).

6. The method of claim 1, further comprising
forming a normalized voxel intensity histogram having the $I_{peak}$ from the normalized voxel intensities; and
filtering the normalized voxel intensity histogram by a wave filter.

7. The method of claim 1, wherein the value is 0.1-0.31.

8. The method of claim 7, wherein the value is 0.2.

9. The method of claim 1, further comprising
pre-screening the voxels by eliminating voxel with the normalized voxel intensity smaller than or equal to the $I_{peak}$; and
performing a fuzzy C-mean clustering on the pre-screened voxels to form a plurality of voxel clusters, wherein each of the voxel clusters has a first average normalized voxel intensity.

10. The method of claim 9, wherein selecting the voxel with the normalized voxel intensity larger than the threshold comprises:
selecting voxel cluster having the first average normalized voxel intensity larger than the threshold to form a candidate voxel cluster;
further dividing the candidate voxel cluster into at least one voxel label, wherein the voxel label has a second average normalized voxel intensity; and
selecting voxel label having the second average normalized voxel intensity larger than the threshold to form a candidate voxel label, wherein the candidate voxel label is the cerebral infarct.

11. The method of claim 10, wherein the voxel dusters comprises 6-100 voxel clusters.

12. The method of claim 11, wherein the voxel dusters comprises 50 voxel dusters.

13. The method of claim 10, wherein further dividing the candidate voxel cluster into the voxel label is based on the location of the voxel label.

14. The method of claim 10, further comprising determining an edge of each voxel label in the image, and eliminating voxel label without the edge to form the candidate voxel label.

15. The method of claim 10, further comprising:
receiving an apparent diffusion coefficient (ADC) map of the brain of the subject from the magnetic resonance imaging scanner, wherein the ADC map has a plurality of ADC voxels, and each of the ADC voxels has an ADC voxel intensity;
registering the ADC map to the image by a rigid registration and calibrating the ADC map; and
normalizing the ADC voxel intensities to make the ADC voxel intensities disperse in a standard range, and to form a normalized ADC voxel intensity histogram.

16. The method of claim 15, further comprising:
determining a peak of the normalized ADC voxel intensity histogram, which the normalized ADC voxel intensity of the peak is $I_{peak,\ ADC}$, and an average normalized ADC voxel intensity of lower half in the voxel label, $I_{lower\ mean,\ ADC}$; and
eliminating voxel label with $I_{lower\ mean,\ ADC}/I_{peak,\ ADC} \geq 0.5$ to form the candidate voxel label.

17. A method for quantifying a cerebral infarct, comprising:
determining the cerebral infarct of an image by the method for detecting the cerebral infarct of claim 1; and
determining cerebral infarct volume based on the cerebral infarct.

* * * * *